United States Patent [19]

Ueda et al.

[11] Patent Number: 5,533,513
[45] Date of Patent: Jul. 9, 1996

[54] EXPIRATION COLLECTOR

[75] Inventors: Hideo Ueda, Osaka; Mitsuo Hiromoto, Kyoto; Meng Gang, Kyoto; Yutaka Yamasaki, Kyoto, all of Japan

[73] Assignee: Kyoto Dai-Ichi Kagaku Co., Ltd., Kyoto, Japan

[21] Appl. No.: 327,908

[22] Filed: Oct. 24, 1994

[30] Foreign Application Priority Data

Oct. 25, 1993 [JP] Japan ................................ 5-290133

[51] Int. Cl.$^6$ .................................................. A61B 5/097
[52] U.S. Cl. .......................... 128/719; 128/730; 73/23.3; 422/84
[58] Field of Search .................................... 128/718, 719, 128/730; 422/84; 73/23.3

[56] References Cited

U.S. PATENT DOCUMENTS

| 3,890,967 | 6/1975 | Elam et al. . | |
|---|---|---|---|
| 4,818,489 | 4/1989 | Gonner et al. | 128/719 |
| 5,042,501 | 8/1991 | Kenny et al. . | |
| 5,060,656 | 10/1991 | Howard . | |
| 5,425,374 | 6/1995 | Ueda et al. | 128/719 |

FOREIGN PATENT DOCUMENTS

| 0548624A1 | 6/1993 | European Pat. Off. . |
|---|---|---|
| WO90/14043 | 11/1990 | WIPO . |
| WO91/07912 | 6/1991 | WIPO . |

*Primary Examiner*—Lee S. Cohen
*Attorney, Agent, or Firm*—Nikaido, Marmelstein, Murray & Oram

[57] ABSTRACT

An expiration suction passage communicating with an expiration blowing part provided with a non-airtight mask is connected to a forward end surface of a syringe through a two-way on-off electromagnetic valve, while an expiration transmission passage communicating with a sample outlet is also connected to the forward end surface of the syringe. A two-way on-off electromagnetic valve is provided in the expiration transmission passage, and an $O_2$ sensor is provided between the electromagnetic valve and the sample outlet as a standard gas sensor. The syringe has a capacity capable of collecting several breaths, and a sucking operation is driven at a speed for collecting several breaths in single suction.

6 Claims, 5 Drawing Sheets

EXPIRATION COLLECTOR

BACKGROUND OF THE INVENTION

1. Field of the Invention

The present invention relates to an expiration collector for collecting expiration from a subject as a sample, for analyzing the expiration sample in an analyzer such as a gas chromatograph.

2. Description of the Background Art

A clinical test for diagnosing, curing or preventing a disease is generally made on blood or urine. On the other hand, expiration is employed in the laboratory level as a specimen for a clinical biochemical test other than those for blood and urine, leading to such recognition that expiration also includes information as to a disease. The expiration test has such an advantage that the expiration can be collected at any time in a painless manner.

Methods of collecting a specimen of expiration for measuring components of the expiration specimen by an analyzer such as a gas chromatograph are roughly classified into three types, i.e., a chemical trap method of blowing expiration into a solvent for dissolving the former in the latter, a cold trap method of blowing a large amount of expiration into a cold trap which is cooled to about −80° C., for example, for condensing the same, and an adsorption trap method of adsorbing expiration components to an adsorption trap which is charged with activated carbon or adsorption resin (Scientific American, July 1992, pp. 52–57). Among these, the cold trap method and the adsorption trap method have already been put into practice.

In the cold trap method, the sample as trapped is generally partially injected into a gas chromatograph through a micro syringe, to be subjected to analysis. However, it is extremely difficult to put this method into practice as clinical test means for a hospital routine which must be quickly and readily carried out while bringing the analyzer into the bedside of a patient.

In the adsorption trap method, expiration components which are adsorbed by the trap are heated and desorbed to be introduced into a gas chromatograph. However, this method is not suitable for a clinical test for a routine which must be quickly and readily carried out while bringing the analyzer into the bedside of a patient either, in addition to such an essential problem that adsorptivity of the adsorption trap is varied with the components.

In expiration which is subjected to analysis, an initial part containing air from a dead space is eliminated so that a part called end-tidal air is most suitably employed as a sample for the analyzer. The end-tidal air, which contains only alveolar air with homogeneous concentration of expiration components, is excellent as a specimen. In an expiration test, therefore, the end-tidal air is measured as the most reliable specimen expressing the state of the subject, while a specific apparatus is required for collecting the end-tidal air.

On the other hand, the method of collecting the expiration by blowing the same into an apparatus is applicable only to a conscious subject. For example, it is difficult to correctly collect expiration from a subject who is unavailable for communication such as a baby, a child, a soporose patient or an unconscious patient. If the subject is healthy but old, for example, it may also be difficult to test the end-tidal air in consideration of his physical strength.

A gas measurer such as a gas chromatograph is now being put into practice as a clinical test appliance with improvement of sensitivity, miniaturization and a technique of implementing portability. When such a gas measurer is applied to an expiration analyzer for carrying out a quick clinical test, it is necessary to simply collect expiration in a gas state without trapping the same by a cold trap or an adsorption trap, for directly guiding the expiration to the analyzer so that reliable test data can be obtained in a short time. In order to attain high practicality of such a clinical test appliance, it is necessary to simplify the operation for collecting expiration which is employed as a specimen.

SUMMARY OF THE INVENTION

An object of the present invention is to provide an expiration collector which can automatically sample expiration and guide the same to an analyzer in a simple operation even if a subject is unavailable for communication, in order to attain a clinical test appliance with an expiration specimen.

The expiration collector according to the present invention comprises an expiration blowing part which is provided on its forward end with a non-airtight mask to be applied to a respiratory organ, and a collecting mechanism communicating with a base end portion of the expiration blowing part and having a suction and discharge mechanism for collecting expiration in a collecting vessel and transmitting the expiration which is collected in the collecting vessel toward an expiration measurer, a passage switching mechanism for switching passages by opening and closing an expiration suction passage from the expiration blowing part to the collection vessel and opening and closing an expiration transmission passage from the collection vessel toward the expiration measurer, heating means for heating the expiration blowing part, the collecting mechanism, the expiration suction passage, the expiration transmission passage and the passage switching mechanism to a temperature exceeding the body temperature of a subject, and a control part for controlling the passage switching mechanism and the collecting mechanism to open the expiration suction passage and close the expiration transmission passage in collection of expiration in the collecting vessel for sucking the expiration in the collecting vessel over a period for a plurality of breaths and to close the expiration suction passage and open the expiration transmission passage in transmission of the expiration for discharging the expiration from the collection vessel.

The non-airtight mask provided on the forward end of the expiration blowing part, which is adapted to cover the respiratory organ including at least one of the mouth and the nose of the subject for sucking expiration from the subject, is provided with pores or clearances or made of an air-permeable material so that the mouth and the nose of the subject is not blocked but the subject can breathe in a normal state. A portion of the expiration blowing part located between the mask and the base end portion is made of an elastic material which is hard to react with or adsorb expiration components. The collecting mechanism is adapted to temporarily store the expiration which is sucked through the expiration blowing part in the collecting vessel, for transmitting the same toward the expiration measurer after expiration gas concentration is homogenized in the collecting vessel. The passage switching mechanism is adapted to switch the passage for sucking and collecting the expiration in the collecting vessel and transmitting the expiration from the collecting vessel.

If moisture which is contained in the expiration is condensed to adhere to the inner wall of the passage for feeding the expiration sample, target components of the expiration are dissolved in the condensed moisture and reduced in amount, to cause incorrect measurement. Therefore, the heating means heats the passage for feeding the expiration sample to a temperature exceeding the body temperature of the subject, thereby preventing condensation of the moisture contained in the expiration.

The expiration is sampled through the non-airtight mask from the subject by suction, and hence ambient air is also incorporated in addition to the expiration. Further, expiration other than that called end-tidal air containing only alveolar air is also incorporated since the expiration is sucked over a period for a plurality of breaths. In order to analyze the expiration which is mixed with that other than the end-tidal air and ambient air for obtaining an analytical value corresponding to the end-tidal air, it is necessary to make correction in relation to dilution of the expiration with the air.

In a preferable mode, a standard gas sensor is provided in the expiration transmission passage for detecting at least either $O_2$ gas or $CO_2$ gas as standard gas for calculating dilution of the expiration sample from standard gas concentration which is detected by the standard gas sensor with reference to standard gas concentration in the end-tidal air, thereby correcting the measured value of expiration componential concentration.

This correction is on the premise of such recognition that $O_2$ concentration and $CO_2$ concentration in end-tidal air are substantially constant regardless of the subject. Even if the expiration sample is diluted with ambient air and air exhaled from a dead space, $O_2$ concentration or $CO_2$ concentration in the expiration sample is measured as standard gas concentration, to obtain the dilution of the expiration sample from the measured value of the standard gas concentration with reference to $O_2$ concentration or $CO_2$ concentration in end-tidal air which is supplied as a constant, thereby correcting the measured value of the expiration componential concentration.

When $O_2$ gas is employed as standard gas, correction is made as follows:

$$[A'] = f_1 \cdot (21-[a_1])[A]/(21-[b_1]) \quad (1)$$

assuming that [A] represents a target componential measured value of the expiration sample, $[b_1]$ (vol. %) represents $O_2$ concentration in the expiration sample, [A'] represents the corrected target componential measured value, $[a_1]$ represents $O_2$ concentration in the end-tidal air which is supplied as a constant such as 15.3, for example, and $f_1$ represents an experimentally prescribed coefficient such as 1.67, for example. The numeral "21" is $O_2$ concentration (vol. %) in the air.

When $CO_2$ gas is employed as standard gas, on the other hand, correction is made as follows:

$$[A'] = f_2 \cdot [a_2][A]/[b_2] \quad (2)$$

assuming that $[b_2]$ represents $CO_2$ concentration in the expiration sample, $[a_2]$ represents $CO_2$ concentration in the end-tidal air which is supplied as a constant such as 4.9, for example, and $f_2$ represents an experimentally prescribed coefficient such as 1.26, for example. Expiration which is temporarily collected and thereafter guided to a measurer for measurement is reduced at a constant rate as compared with that directly guided to the measurer for measurement. The coefficients $f_1$ and $f_2$, which are adapted to correct such reduction caused in this method, are preferably obtained every specification, since the coefficients are varied with the gas components as measured and the structure of the apparatus.

According to the present invention, it is possible to collect expiration for several breaths for transmitting the same to the expiration measurer while allowing normal breathing of the subject by simply applying the mask of the expiration blowing part to the mouth and the nose of the subject and starting collection. Thus, it is possible to automatically collect expiration of not only a normal but a subject who is unavailable for communication such as an unconscious patient or an infant. The collecting vessel can average several breathes for transmitting the expiration to the measurer, whereby it is possible to obtain a reproducible measured value.

When the sensor for detecting at least either $O_2$ or $CO_2$ is provided in the expiration transmission passage, it is possible to obtain highly reliable expiration componential concentration by correcting the measured value of the expiration sample diluted with ambient air and expiration other than alveolar air.

When the inventive expiration collector is connected with an expiration analyzer, it is possible to analyze expiration while omitting complicated operations. Alternatively, the inventive expiration collector can be employed as an independent automatic collector.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
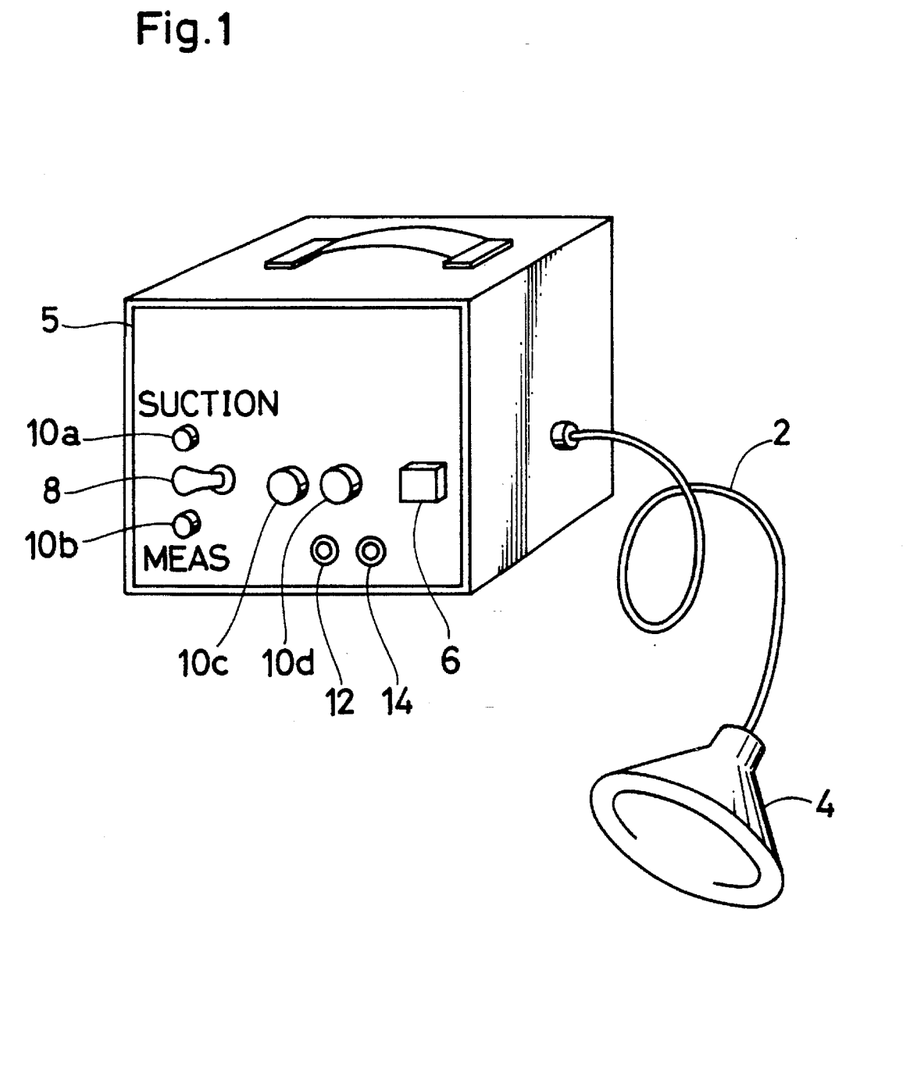
FIG. 1 is a perspective view showing the appearance of an embodiment of the present invention.

FIG. 1 is a perspective view showing the appearance of an expiration collector according to an embodiment of the present invention. An expiration blowing part 2 has a forward end portion which is provided with a non-airtight mask 4, and a base end portion which is connected to a collector body 5. The body 5 stores a collecting mechanism and other mechanisms of the present invention. A power supply switch 6, a transfer switch 8 for switching the operation mode between a suction mode and a transmission mode, and display lamps 10a, 10b, 10c and 10d for displaying the operation modes are provided on a front panel of the body 5. The display lamps 10a and 10b are adapted to indicate the suction mode ("Suction") and the transmission mode ("Meas.") respectively. The display lamp 10c indicates whether it is possible ("Ready") or impossible ("Wait") to command a subsequent operation by changing its color, and the display lamp 10d displays performance of temperature control by heating means for preventing moisture contained in expiration from being condensed on a passage. A gas connection port 12 is connected with an expiration measurer through a pipe for supplying an expiration sample which is collected by this collector to the expiration measurer, and a signal connection port 14 is adapted to transfer electric signals between the collector and the expiration measurer.

Figure 2:
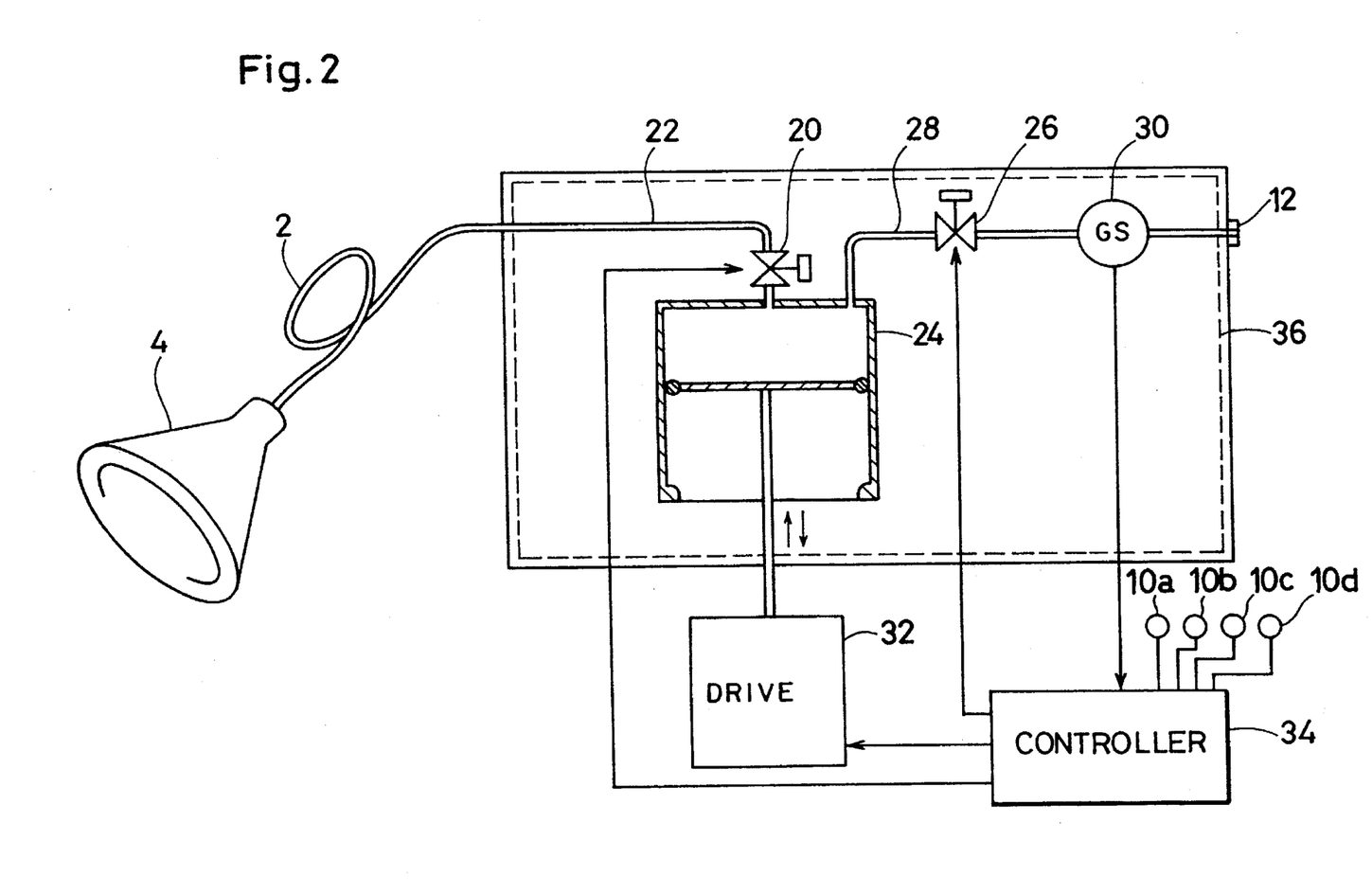
FIG. 2 is a sectional view showing a principal part of the embodiment according to the present invention.

With reference to FIG. 2, the internal mechanism of this embodiment is described in more detail. A tube forming the expiration blowing part 2 is prepared from polytetrafluoroethylene as an elastic material neither reacting with nor adsorbing expiration components, and a heater which is so temperature-controlled that its inner wall temperature is 40° to 50° C. is wound on this tube. The mask 4 is mounted on a forward end of this tube with a clearance defined therebetween so that a subject can normally breathe when the mask 4 is applied to the subject's mouth and nose.

The base end portion of the expiration blowing part 2 communicates with an expiration suction passage 22, which is provided in the collector body 5 and connected to a forward end surface of a syringe 24 through a two-way on-off electromagnetic valve 20. An expiration transmission passage 28 communicating with a sample outlet 12 is also connected to the forward end surface of the syringe 24. This expiration transmission passage 28 is provided with another two-way on-off electromagnetic valve 26, and an $O_2$ sensor is provided between the two-way on-off electromagnetic valve 26 and the sample outlet 12 as a standard gas sensor 30. The standard gas sensor 30 may alternatively be formed by a $CO_2$ sensor, or a sensor which can detect both of $O_2$ and $CO_2$. This gas sensor 30 is adapted to correct expiration components diluted with ambient air and expiration other than alveolar air which are incorporated from the expiration blowing part 2 with the expiration, by using equations (1) or (2).

The syringe 24 has a capacity capable of collecting several breaths, such as 1 to 3 liters, for example. A driving mechanism 32 comprising a motor as a driving source drives the syringe 24 in directions for pushing and retracting its piston.

The expiration suction passage 22, the syringe 24 and the expiration transmission passage 28 are stored in a thermostat 36, and controlled to be at a constant temperature of 40° to 50° C.

A controller 34 is adapted to control switching operations of the electromagnetic valves 20 and 26, the operation of the syringe 24, and lighting of the display lamps 10a to 10d. In order to suck an expiration sample in the syringe 24 to collect the same, the mask 4 is applied to the respiratory organ of the subject for continuously collecting several breaths while opening and closing the electromagnetic valves 20 and 26 respectively. In order to average the breaths as collected, the driving mechanism 32 retracts the piston of the syringe 24 over 1 minute by a command from the controller 34, so that the syringe 24 is filled up with the expiration sample in this period. In order to transmit the expiration sample which is collected in the syringe 24 to the expiration measurer, the driving mechanism 32 drives the piston for entirely transmitting the expiration sample collected in the syringe 24 in about 6 seconds while closing and opening the electromagnetic valves 20 and 26 respectively. In a purge mode which is prepared for washing the passage for the expiration with air after the expiration sample is transmitted from the syringe 24, the piston of the syringe 24 is reciprocated 3 to 5 times while opening and closing the electromagnetic valves 20 and 26 respectively.

Figure 3:
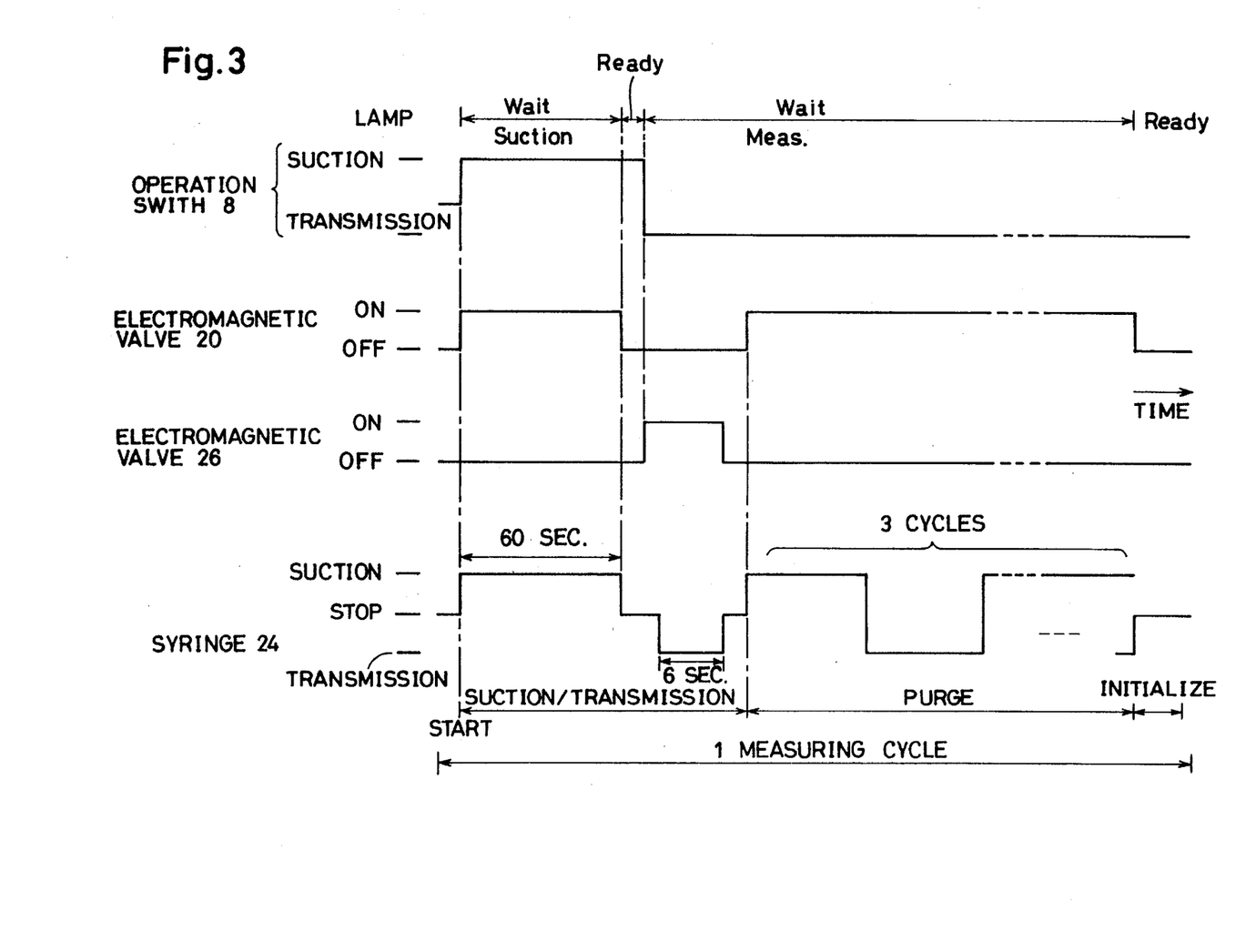
FIG. 3 is a timing chart showing the operation of the embodiment shown in FIG. 2.

With reference to FIG. 3, the operation of this embodiment is described in detail.

In order to collect expiration, the mask 4 is applied to the mouth and the nose of the subject, and the transfer switch 8 is switched toward a suction side to apply power. The electromagnetic valves 20 and 26 are opened (on) and closed (off) respectively, and the driving mechanism 32 retracts the piston of the syringe 24 so that the expiration is sucked into the syringe 24 with ambient air. When this suction is continued for 1 minute, the operation of the syringe 24 is stopped and the electromagnetic valve 20 is closed. Then the lamp 10c is switched from "Wait" to "Ready".

When the operator switches the transfer switch 8 toward the transmission (Meas.) side, the electromagnetic valve 26 is opened and the driving mechanism 32 pushes the piston of the syringe 24 upon a lapse of several seconds. After the piston is so pushed as to entirely transmit the expiration sample from the syringe 24 in 6 seconds, the syringe 24 is stopped and the electromagnetic valve 26 is closed. Thus, the expiration sample is completely transmitted.

A purge mode operation is started upon a lapse of several seconds. The electromagnetic valve 20 is opened to repeat the sucking and transmitting operation of the syringe 24 three times. Thereafter the collector enters an initial state to be prepared for next expiration collecting.

Figure 4:
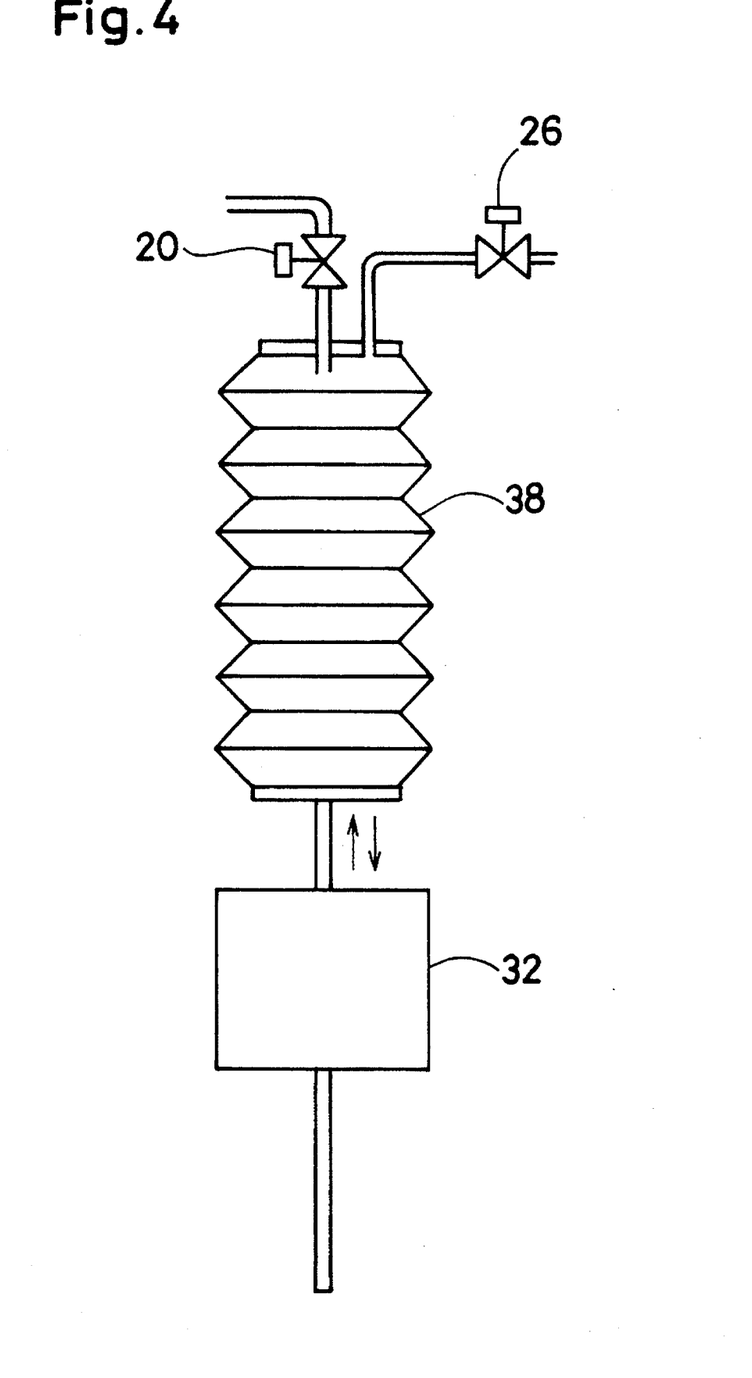
FIG. 4 is a sectional view showing a bellows type vessel which can be employed in place of a syringe provided in the embodiment shown in FIG. 2.

The syringe 24 provided in the embodiment shown in FIG. 2 can alternatively be replaced by a bellows type vessel 38 shown in FIG. 4. A driving mechanism 32 comprising a motor expands and contracts the vessel 38 to suck and transmit expiration. The operation of this vessel 38 is identical to that of the embodiment shown in FIG. 2, and suction, transmission and purge modes are controlled at the timing shown in FIG. 3.

Such a bellows type vessel 38 has excellent durability.

Figure 5:
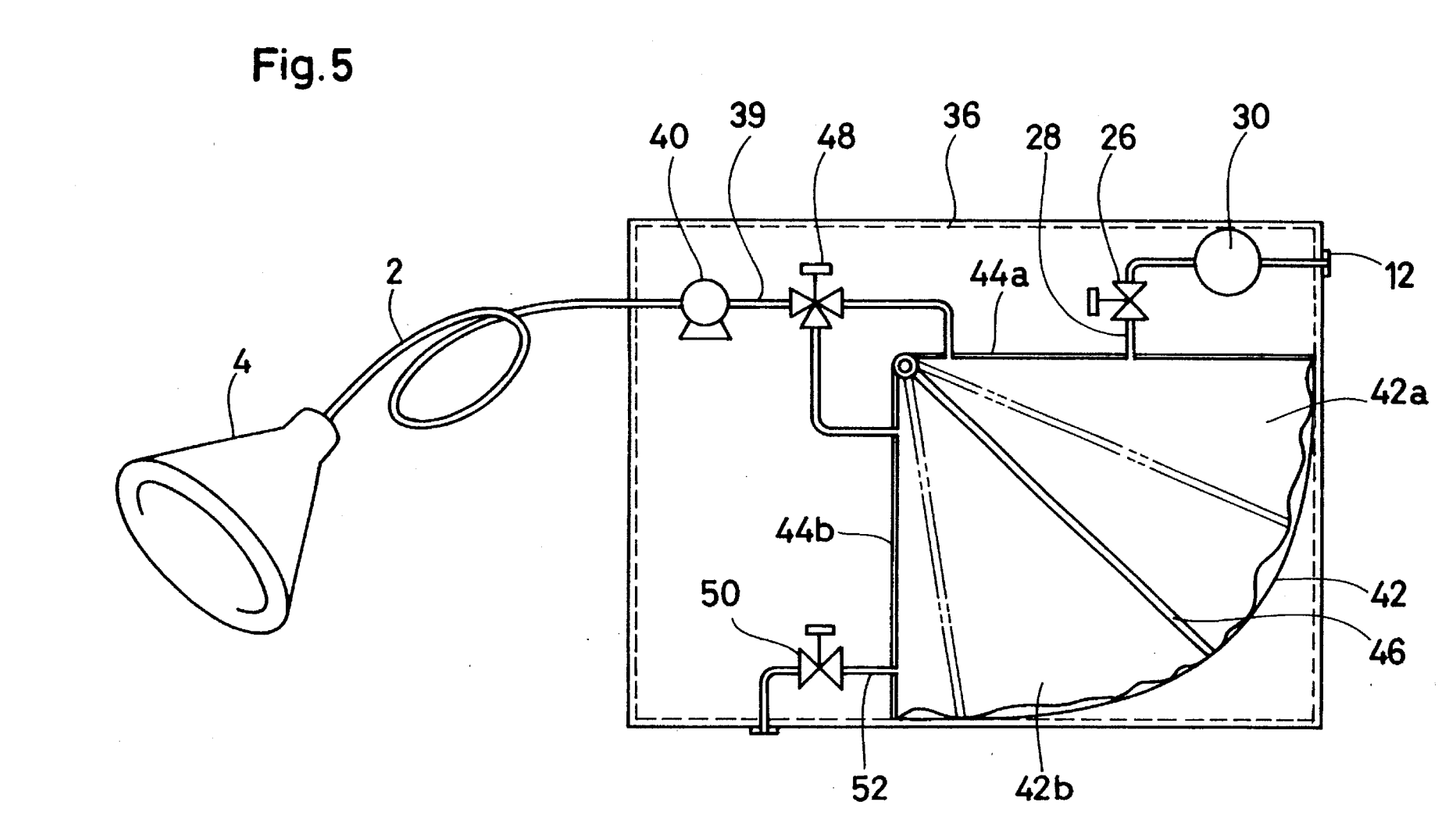
FIG. 5 is a sectional view showing a principal part of another embodiment of the present invention.

FIG. 5 shows another embodiment of the present invention. In order to suck and collect expiration from an expiration blowing part 2, a collecting pump 40 is provided in an expiration suction passage 39 which communicates with the expiration blowing part 2. The collecting pump 40 is suitably formed by a diaphragm pump having a flow rate of about 1 to 5 liters/min. In a collecting vessel 42, only two wall surfaces 44a and 44b having single sides in common are fixed while remaining wall surfaces are formed by bellows type ones. This collecting vessel 42 is partitioned into a sample chamber 42a and an atmosphere chamber 42b by a movable plate 46 which is mounted to be rotatable about the common side of the fixed wall surfaces 44a and 44b. A three-way electromagnetic valve 48 is provided downstream the collecting pump 40 so that outlets thereof are connected to the sample chamber 42a and the atmosphere chamber 42b respectively. The sample chamber 42a is connected with an expiration transmission passage 28 which communicates with a sample outlet 12 and comprises a two-way on-off electromagnetic valve 26 and a standard gas sensor 30 for detecting at least either $O_2$ or $CO_2$. On the other hand, the atmosphere chamber 42b is connected with a discharge passage 52 comprising another two-way on-off electromagnetic valve 50.

Also in this embodiment, an expiration blowing part 2 is heated while the collecting pump 40, the three-way electromagnetic valve 48, the collecting vessel 42 and the expiration transmission passage 28 are stored in a thermostat 36 and heated to 40° to 50° C. The capacity of the collecting vessel 42 is about 2 liters in total of those of the collecting chamber 42a and the atmosphere chamber 42b.

In order to collect expiration in the embodiment shown in FIG. 5, the three-way electromagnetic valve 48 is switched to connect the collecting pump 40 with the sample chamber 42a and the electromagnetic valves 26 and 50 are closed and opened respectively so that the collecting pump 40 is driven to transmit expiration to the sample chamber 42a from a mask 4 with air. The collecting pump 40 operates for about 1 minute to collect the expiration while spreading the sample chamber 42a. At this time, the atmosphere chamber 42b is contracted while discharging air which has been contained therein through the discharge passage 52.

In order to transmit the expiration sample which is collected in the sample chamber 42a, the electromagnetic valves 26 and 50 are opened and closed respectively so that the three-way electromagnetic valve 48 is switched to connect the collecting pump 40 with the atmosphere chamber 42b. At this time, the expiration or air received from the collecting pump 40 enters the atmosphere chamber 42b to expand the same, whereby the sample chamber 42a is contracted so that the expiration sample which has been stored therein is transmitted to an expiration measurer through the sample outlet 12.

In order to perform a purge operation after transmitting the expiration sample from the sample chamber 42a, the three-way electromagnetic valve 48 is switched toward the sample chamber 42a while separating the mask 4 from the subject, and the electromagnetic valve 26 is opened to drive the collecting pump 40 continuously for several minutes. At this time, air which is sucked from the expiration blowing part 2 passes through the sample chamber 42a to be discharged through the expiration transmission passage 28, thereby washing the passage for the expiration sample.

The present invention is not restricted to the embodiments shown in FIGS. 2 to 5, but may be modified in various manners.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. An expiration collector comprising:

an expiration measurer;

a non-airtight mask to be applied to a respiratory organ;

an expiration blowing part being provided on a forward end with said non-airtight mask;

an expiration suction passage connected to said expiration blowing part;

a collecting mechanism connected to said expiration suction passage and communicating with a base end portion of said expiration blowing part, and said collecting mechanism having a collecting vessel and a suction and discharge mechanism for collecting expiration in said collecting vessel and for transmitting said expiration being collected in said collecting vessel toward said expiration measurer;

an expiration transmission passage connected to said collecting vessel and said expiration measurer;

a passage switching mechanism for switching passages by a) a first switch means for, opening and closing said expiration suction passage from said expiration blowing part to said collecting vessel and b) a second switch means for opening and closing said expiration transmission passage from said collecting vessel toward said expiration measurer;

heating means for heating said expiration blowing part, said collecting mechanism, said expiration suction passage, said expiration transmission passage and said passage switching mechanism to a temperature exceeding a body temperature of a subject; and a control part, connected to said first and second switch means and said collecting mechanism, for controlling said passage switching mechanism and said collecting mechanism a) by controlling said first switch means to open said expiration suction passage and by controlling said second switch means to close said expiration transmission passage in collection of expiration in said collecting vessel wherein said expiration is sucked into said collecting vessel over a period of a plurality of breaths and b) by controlling said first switch means to close said expiration suction passage and by controlling said second switch means to open said expiration transmission passage in transmission of said expiration wherein said expiration is discharged from said collecting vessel.

2. An expiration collector in accordance with claim 1, wherein a standard gas sensor is provided in said expiration transmission passage for detecting at least one of $O_2$ gas and $CO_2$ gas as standard gas so that dilution of an expiration sample is calculated from standard gas concentration being detected by said standard gas sensor with reference to standard gas concentration in end-tidal air, thereby correcting a measured value of expiration componential concentration.

3. An expiration collector in accordance with claim 1, wherein said control part for controlling said passage switching mechanism and said collecting mechanism in a purge mode by sucking air from said expiration blowing part and introducing said air into said passages and said collecting vessel for feeding said expiration, therein purging said passages and said collecting vessel with said air.

4. An expiration collector in accordance with claim 1, wherein said collecting mechanism is a syringe comprising a driving source being controlled by said control part, so that said expiration suction passage and said expiration transmission passage are connected to a forward end portion of said syringe, said passages being provided with switching valves therefor as said passage switching mechanism.

5. An expiration collector in accordance with claim 1, wherein said collecting mechanism is a bellows type vessel of a variable volume having a driving source being controlled by said control part in its base end portion, so that said expiration suction passage and said expiration transmission passage are connected to a forward end portion of said vessel, said passages being provided with switching valves therefor as said passage switching mechanism.

6. An expiration collector in accordance with claim 1, wherein a space of a constant volume of said collecting mechanism is partitioned into a sample chamber and an atmosphere chamber by a movable plate so that said expiration transmission passage is connected to said sample chamber and a first on-off valve partially forming said passage switching mechanism is provided in said expiration transmission passage while a discharge passage comprising a second on-off valve is connected to said atmosphere chamber, said collecting mechanism further comprising a suction pump communicating with said expiration blowing part, and a switching valve partially forming said passage switching mechanism for switching to connect an outlet of said suction pump to either said sample chamber or said atmosphere chamber, and said control part allows said suction pump to communicate with said sample chamber by said switching valve, closing said first on-off valve and opening said second on-off valve in collection of said expiration in said sample chamber while allowing said suction pump to communicate with said atmosphere chamber by said switching valve, opening said first on-off valve and closing said second on-off valve in transmission of an expiration sample from said sample chamber.

\* \* \* \* \*